United States Patent [19]

Kubela et al.

[11] 4,138,494

[45] Feb. 6, 1979

[54] 3-PHENYLINDOLINES

[75] Inventors: Rudolf Kubela, Cote St. Luc; Vaclav Musil; Lise A. Hughes, both of Ville-de-Lery, all of Canada

[73] Assignee: Delmar Chemicals Limited, LaSalle, Canada

[21] Appl. No.: 741,665

[22] Filed: Nov. 15, 1976

Related U.S. Application Data

[62] Division of Ser. No. 589,402, Jun. 23, 1975, Pat. No. 4,080,330.

[51] Int. Cl.² .................... A61K 31/40; C07D 209/04
[52] U.S. Cl. ............................ 424/274; 260/326.11 R
[58] Field of Search ................ 260/326.11 R; 424/274

[56]  References Cited

U.S. PATENT DOCUMENTS 3,732,236   5/1972   Wu et al. .................... 424/274 X
3,989,714   11/1976  Klutcko et al. ............. 260/326.11 R

FOREIGN PATENT DOCUMENTS 4745344  11/1972  Japan.

*Primary Examiner*—Ethel G. Love
*Attorney, Agent, or Firm*—Fisher, Christen & Sabol

[57]  ABSTRACT

The present invention is concerned with novel 2-unsubstituted-3-phenylindolines and acid addition salts thereof. These compounds have been found to have a valuable pharmacological property indicative of possible utility in controlling coagulation of the blood.

10 Claims, No Drawings

3-PHENYLINDOLINES

This is a division of application Ser. No. 589,402, filed June 23, 1975, now U.S. Pat. No. 4,080,330.

FIELD OF INVENTION

The present invention relates to novel substituted and unsubstituted 3-phenylindolines, processes for the production thereof and pharmaceutical compositions containing such compounds as active ingredient.

BACKGROUND OF INVENTION

Certain 3-substituted indolines are known in the art, and various methods have been employed for their preparation. Furthermore, whilst some 3-phenylindolines are known, to the best of our knowledge, all such compounds are either simultaneously substituted in the 2-position and/or carry an additional substituent in the 3-position. The indolines of the present invention are characterized by being unsubstituted in the 2-position and substituted only by a phenyl residue in the 3-position.

SUMMARY OF INVENTION

The present invention in a composition of matter aspect provides novel 2-unsubstituted-3-phenylidolines having the following general formula:

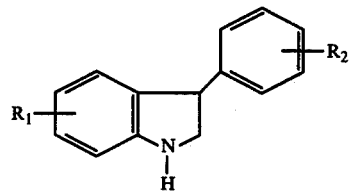

wherein $R_1$ and $R_2$ individually represent hydrogen, halogen, lower alkoxy or lower alkyl, preferably hydrogen or halogen; $R_1$ being in the 5-, 6- or 7- position only. Also within the scope of this invention are the non-toxic acid addition salts of the novel 3-phenylindolines which contain basic nitrogen. It has been found that the compounds of the present invention possess a valuable property as indicated by standard pharmacological tests with animals, indicative of possible use in controlling coagulation of the blood, with an acceptable toxicity level.

Furthermore, the novel compounds of this invention are useful as intermediates in the preparation of pharmacologically valuable, novel N-substituted-3-phenylindolines of the following general formula II:

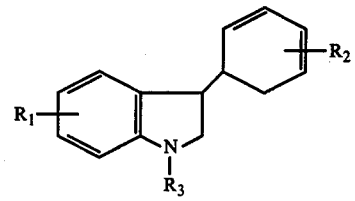

wherein $R_1$ and $R_2$ are as defined above for formula I and $R_3$ represents a moiety of formula

wherein $R_4$ is aminoalkyl of formula

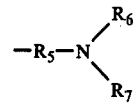

wherein $R_5$ is a straight or branched chain alkyl group; $R_6$ and $R_7$ individually represent hydrogen; lower alkyl; or $R_6$ and $R_7$ together with nitrogen and, optionally an oxygen or further nitrogen, represent one of morpholine, piperazine, piperidine and pyrrolidine and pharmaceutically acceptable addition salts thereof with inorganic or organic acids.

The compounds of the above formula II are more fully described and claimed in the specification of our copending application Ser. No. 589,402 mentioned hereinbefore.

DETAILED DESCRIPTION OF INVENTION

The present invention provides novel 3-phenylindolines of the general formula I:

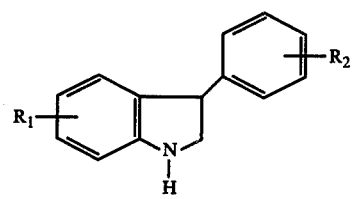

wherein $R_1$ and $R_2$ individually represents hydrogen, halogen, lower alkoxy or lower alkyl; $R_1$ being in the 5-, 6- or 7-position only and pharmaceutically acceptable addition salts thereof with inorganic or organic acids.

It will be noted that the compounds of formula I above have an assymetric centre at $C_3$ and these compounds may therefore exist as optical isomers. The connotation of the general formulae presented herein is to include all such isomers either separated or in racemic mixtures, the latter being indicated throughout the text unless otherwise specified.

The term "halogen" as used throughout the present specification refers to fluorine, chlorine or bromine, especially chlorine and fluorine. The term "lower" when used throughout this specification to qualify organic groups, means such groups having at most six, preferably at most four, and especially one or two, carbon atoms. Examples of lower alkyl groups include methyl, ethyl, propyl, isopropyl, butyl, isobutyl secondary and tertiary butyl and the various pentyl and hexyl isomers. Examples of lower alkenyl are vinyl, 1-propenyl, 2-propenyl (vinyl), 1-isobutenyl and 1-hexenyl.

The novel 3-phenylindolines of the present invention are prepared by reduction of suitable 3-phenylindoles.

In a preferred process, the compounds of the formula I:

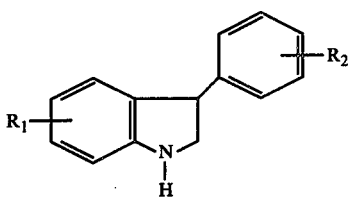

wherein $R_1$ and $R_2$ are as defined hereinbefore are prepared by reducing in a strongly acid medium a 3-phenylindole of formula III:

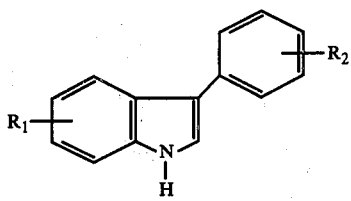

wherein $R_1$ and $R_2$ are as defined above for formula I.

The required conditions may be conveniently provided by effecting the reaction in the presence of a strong protonating agent, such mineral acids, for example, as hydrochloric acid, hydrofluoroboric acid or σ-phosphoric acid, or Lewis acids, such as borontrifluoride, aluminium trichloride and zinc dichloride in the presence of an organic acid, such as glacial acetic acid, propionic acid, trifluoroacetic acid and formic acid being suitable.

Reduction of the indole to the corresponding indoline may be effected catalytically utilizing a hydrogenation procedure in the presence of a suitable catalyst, such as platinum or palladium. Examples of such reducing systems include hydrofluoroboric acid/platinum oxide and hydrofluoroboric acid/palladium-charcoal in lower alcohols as solvent.

Alternatively, a strongly acidic chemical reducing system may be used, examples thereof being boron trifluoride/zinc dust/glacial acetic acid and zinc dust/hydrochloric acid.

As stated previously, the compounds of the present invention may exist in two isomeric forms. The processes described above produce a racemic mixture of the two possible isomers. If the mixture of isomers obtained as the product in any specific reaction is not utilizable in that form due to the undesirable presence of one isomer, the isomers may be resolved by standard techniques generally utilizing differences in the physical and/or chemical properties between the isomers, such as relative solubilities etc.

The 3-phenylindolines of formula I form acid addition salts with various inorganic or organic acids and such salts are included within the scope of the present invention. Of special interest are the pharmaceutically acceptable acid addition salts which are usually more convenient to handle than the free compounds of formula I. Acids which form such salts include hydrochloric acid, hydrobromic acid, sulfuric acid, phosphoric acid, nitric acid, acetic acid, maleic acid, fumaric acid, tartaric acid, succinic acid, citric acid, camphorsulfonic acid, ethanesulfonic acid, ascorbic acid and lactic acid. The said salts are prepared by standard procedures usually involving treating the free base with an ethanolic solution of the desired acid, the acid addition salt being obtained generally in the form of a crystalline solid.

The starting materials, namely, the 3-phenylindoles of formula III:

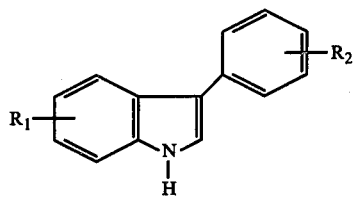

wherein $R_1$ and $R_2$ are as defined above for formula I are either known compounds or may be prepared in a similar manner to the processes for producing the known compounds. Generally, compounds of formula III may be prepared by the Fisher Indole synthesis involving the reaction of a (possibly substituted) phenyl hydrazine with an optionally substituted phenylacetaldehyde in the presence of a strong mineral or Lewis acid, such as zinc chloride, the reaction proceeding via a phenyl hydrazone intermediate as follows:

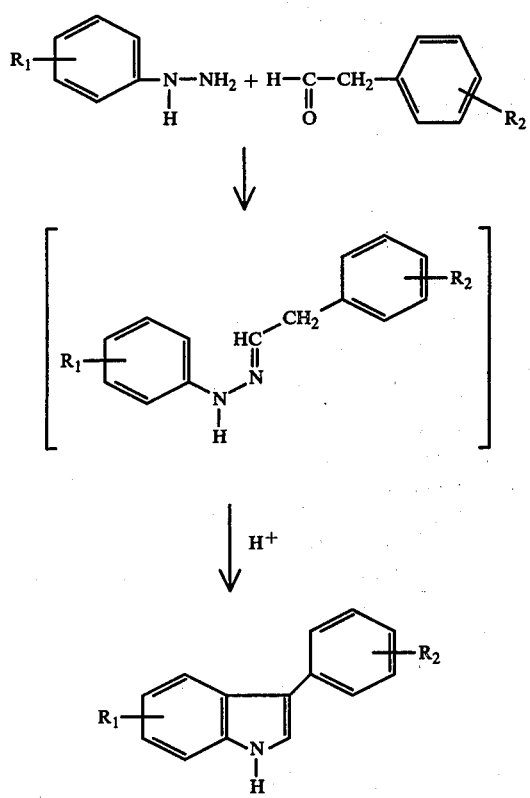

wherein $R_1$ and $R_2$ as defined above for formula I.

The starting 3-phenylindoles may also be prepared by a modification of the above process which comprises reacting an optionally substituent phenylhydrazine hydrochloride with, for example, a dimethyl or diethyl acetal of a phenylacetaldehyde in alcohol.

As indicated previously the novel 3-phenyl-indolines of the present invention possess a useful biological property. For example, 3-phenylindoline itself gave strong indications via a standard platelet aggregation test evaluation (J. Lab. & Clin. Med. 64, 548–559 (1964)) of utility in preventing blood clot formation. The following table summarizes the results in the said test for the above compound. The results obtained in the same test for the known drug, aspirin, were included as a comparison. Test values in excess of 50 are considered pharmacologically significant.

| Compound | Dose a/ml | Result |
|---|---|---|
| 3-phenylindoline | 1 | 100 |
| Aspirin | 5 | 78 |

The present invention further provides in another of its aspects a pharmaceutical composition comprising as an essential active ingredient at least one active compound of formula I or a pharmaceutically acceptable acid addition salt thereof in association with a pharmaceutically acceptable carrier therefor.

The compositions of the present invention are preferably administered orally, rectally or parenterally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage units form" as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

Usually the compositions of this invention contain the active ingredient in an amount of at least 0.5% by weight based on the total weight of the composition and not more than 95% by weight. Conveniently, the compositions of the invention when in dosage unit form contain 0.5 mg to 350 mg, and more conveniently from 5 mg to 250 mg of the active ingredient of formula I.

The compositions of the present invention will normally consist of at least one compound of formula I or a pharmaceutically acceptable acid addition salt thereof, admixed with a carrier, or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semi-solid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, cocoa butter, oil of theobroma, alginates, tragacanth, gelatin, syrup B.P., methyl cellulose, polyoxyethylene sorbitan monolaurate, and methyl and propyl hydroxybenzoates. The choice of carrier is determined by the preferred form of administration, the solubility of the compound and standard pharmaceutical practice, all as more clearly set forth in "Remington's Practice of Pharmacy" by E. W. Martin and E. F. Cook, a well-known reference work in this field. In the case of tablets, a lubricant may be incorporated to prevent sticking and binding of the powdered ingredients in the dies and on the punch of the tabletting machine. For such purpose, there may be employed, for example, talc, aluminum, magnesium or calcium stearates or polyethylene glycols "Carbowaxes" (Registered Trade Mark) of suitable molecular weight.

The pharmaceutical compositions of this invention may contain, in addition to the active 3-phenylindoline ingredient, one or more other physiologically active ingredients which elicit desirable complementary effects.

An example of a suitable pharmaceutical preparation according to the present invention is presented below for the purposes of facilitating a better understanding of this aspect of the invention.

Preparation

Capsules, made up in the usual manner may have the following composition:

| Ingredient | Amount (mg) |
|---|---|
| 3-Phenylindoline | 250 |
| Magnesium stearate | 5 |
| Lactose | 145 |

The present invention will be further described with reference to, but not limited by, the following specific examples.

EXAMPLE 1

3-Phenylindoline and the Monohydrochloride Thereof

A mixture of 50 g of 3-phenylindole, 500 ml of glacial acetic acid, 100 ml of boron trifluoride etherate and 100 g of zinc dust was heated to reflux and, under vigorous stirring, the low volatile components were continuously distilled off until the temperature reached 100° C. The reflux had continued for 90 minutes. After cooling, the reaction mixture was filtered to remove the zinc and zinc salts and the filter cake washed with ether. The filtrate was diluted with 500 ml of water and under cooling 200 ml of 50% aqueous sodium hydroxide was added dropwise. The organic layer was separated and the aqueous phase extracted with ether. The ether extracts were combined and washed with 125 ml of 18% aqueous hydrochloric acid. The aqueous phase was basified with sodium hydroxide to pH 8–9 and extracted with ether. After removal of the solvent from the combined ether extracts, 30.1 g of dark oil was obtained which when distilled at 150° C./0.45 mm Hg gave 26.2 g of the desired 3-phenylindoline as a pale yellow viscous oil.

The monohydrochloride of 3-phenylindoline was found to have a melting point of 140–1° C.

EXAMPLE 2

3-Phenylindoline 8.0 g of 3-phenylindole was dissolved in 120 ml of 96% ethanol and 60 ml of 48% hydrofluoroboric acid was added thereto. 0.4 g of platinum oxide was added to the mixture which was hydrogenated at 30 p.s.i. at room temperature for four hours. The catalyst was removed by filtration, the filtrate concentrated to one-third of the volume, basified with 50% aqueous sodium hydroxide and then extracted with ether. 6.7 g of a dark oil which was obtained from the ether extracts after removal of the solvent was chromatographed on silica gel to give 4.1 g of 3-phenylindoline as a pale yellow viscous oil.

EXAMPLE 3

3-Phenylindoline

A mixture of 4.0 g of 3-phenylindole, 80 ml of 86% ethanol, 35 ml of 48% hydrofluoroboric acid and 0.25 g of 10% Pd/C was hydrogenated at 60 p.s.i. and 60° C. for 18 hours. The reaction mixture was worked up as in Example 2 and 1.9 g of pure 3-phenylindoline was obtained.

EXAMPLE 4

3-Phenylindoline 1.3 g of 3-phenylindole was suspended in 100 ml of 20% aqueous hydrochloric acid. The mixture was heated to 60° C. while stirring vigorously and 20 g of zinc dust was added thereto in small portions over a period of 45 minutes. On completing the addition of zinc dust, the reaction mixture was heated to 100° C. and maintained at this temperature for one hour, filtered hot, and the filtrate cooled to room temperature and washed with ether. The aqueous layer was basified with 50% aqueous sodium hydroxide and the desired product was extracted with ether and then purified by column chromatography using silica gel. The 3-phenylindoline was obtained in a yield of 0.8 g as a yellow viscous oil.

EXAMPLE 5

3-P-chlorophenylindoline

Using the same procedure as detailed in Example 1 3.5 g of 3-p-chlorophenylindole, 35 ml of glacial acetic acid, 7 ml of boron trifluoride etherate and 7 g of zinc dust were reacted together and the product worked up as in Example 1. In this way 1.5 g of the desired 3-p-chlorophenylindoline was obtained as a yellow oil.

Using the general procedures described in detail in the foregoing Examples with, of course, the appropriate choice of starting materials the compounds of the following restricted formula I were prepared. The substituent $R_2$ in the formula is in the para position unless stated otherwise. The melting point given is that of the corresponding hydrochloride unless otherwise stated.

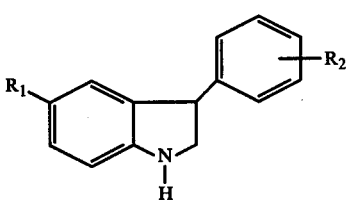

| Example No. | $R_1$ | $R_2$ | $R_3$ | Melting Point |
|---|---|---|---|---|
| 6 | F | F | H | 135–137° C |
| 7 | CH$_3$O | Cl | H | 203–205° C |
| 8 | H | m-F | H | 132–135° C |

Further compounds according to the present invention are as follows:

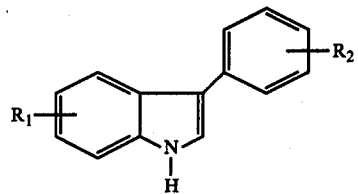

| Example No. | $R_1$ | $R_2$ | $R_3$ |
|---|---|---|---|
| 9 | 6-Cl | m-OCH$_3$ | H |
| 10 | 6-Br | m-CH$_3$ | H |
| 11 | 5-CH$_3$ | m-Cl | H |
| 12 | 5-OC$_2$H$_5$ | o-CH$_3$ | H |
| 13 | 5-OCH$_3$ | o-C$_2$H$_5$ | H |
| 14 | 7-Cl | H | H |
| 15 | 7-Br | p-Cl | H |
| 16 | 7-Cl | p-CH$_3$ | H |
| 17 | 5-CH$_2$CH$_3$ | p-Br | H |
| 18 | 6-CH$_3$ | H | H |

What is claimed is:

1. A 3-phenylindoline having the following general formula:

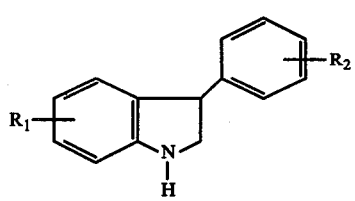

wherein $R_1$ and $R_2$ individually represents hydrogen, halogen, lower alkoxy or lower alkyl, or a pharmaceutically acceptable addition salt thereof with an inorganic or organic acid.

2. A compound as claimed in claim 1 which is 3-phenylindoline or a pharmaceutically acceptable addition salt thereof with an inorganic or organic acid.

3. A compound as claimed in claim 1 which is 3-phenylindoline.

4. A compound as claimed in claim 1 wherein $R_1$ is in the 5-, 6- or 7-position.

5. A compound as claimed in claim 1 wherein $R_1$ and $R_2$ are each halogen.

6. A pharmaceutical composition for controlling coagulation of the blood containing as active ingredient an anti-blood clot formation effective amount of a 3-pheny-lindoline of formula I as defined in claim 1 or a pharmaceutically acceptable addition salt thereof with an inorganic or organic acid.

7. A pharmaceutical composition as claimed in claim 6 wherein the compound is 3-phenylindoline or a pharmaceutically acceptable addition salt thereof with an inorganic or organic acid.

8. A pharmaceutical composition as claimed in claim 6 wherein the compound is 3-phenylindoline.

9. A pharmaceutical composition as claimed in claim 6 wherein $R_1$ is in the 5-, 6- or 7-position.

10. A pharmaceutical composition as claimed in claim 6 wherein $R_1$ and $R_2$ are each halogen.